(12) United States Patent
Cao et al.

(10) Patent No.: US 11,344,243 B2
(45) Date of Patent: May 31, 2022

(54) ARTIFICIAL INTELLIGENCE SELF-LEARNING-BASED STATIC ELECTROCARDIOGRAPHY ANALYSIS METHOD AND APPARATUS

(71) Applicant: Shanghai Lepu CloudMed Co., Ltd, Shanghai (CN)

(72) Inventors: Jun Cao, Beijing (CN); Kaifeng Zang, Beijing (CN); Youchao Lu, Beijing (CN); Pengfei Zhao, Beijing (CN); Erbin Wang, Beijing (CN); Chang Liu, Beijing (CN)

(73) Assignee: Shanghai Lepu CloudMed Co., Ltd, Shanghai (CN)

( * ) Notice: Subject to any disclaimer, the term of this patent is extended or adjusted under 35 U.S.C. 154(b) by 137 days.

(21) Appl. No.: 16/651,890

(22) PCT Filed: Jan. 12, 2018

(86) PCT No.: PCT/CN2018/072362
§ 371 (c)(1),
(2) Date: Mar. 27, 2020

(87) PCT Pub. No.: WO2019/100566
PCT Pub. Date: May 31, 2019

(65) Prior Publication Data
US 2020/0260979 A1 Aug. 20, 2020

(30) Foreign Application Priority Data

Nov. 27, 2017 (CN) .......................... 201711203758.5

(51) Int. Cl.
*A61B 5/316* (2021.01)
*A61B 5/00* (2006.01)
(Continued)

(52) U.S. Cl.
CPC .............. *A61B 5/316* (2021.01); *A61B 5/352* (2021.01); *A61B 5/364* (2021.01); *A61B 5/366* (2021.01);
(Continued)

(58) Field of Classification Search
CPC ......... A61B 5/315; A61B 5/364; A61B 5/352; A61B 5/7203; A61B 5/7225; A61B 5/7267; A61B 5/7271
See application file for complete search history.

(56) References Cited

U.S. PATENT DOCUMENTS

2004/0230105 A1 11/2004 Geva et al.
2017/0360377 A1* 12/2017 Rossi ..................... A61B 5/364

FOREIGN PATENT DOCUMENTS

CN 105411567 B 3/2016
CN 105748063 A 7/2016
(Continued)

OTHER PUBLICATIONS

Acharya et al., A Deep Convolutional Neural Network Model to Classify Heartbeats, Comput Biol. Med., vol. 89, (Oct. 1, 2017, pp. 389-396, abstract only.
(Continued)

*Primary Examiner* — Catherine M Voorhees
*Assistant Examiner* — Roland Dinga
(74) *Attorney, Agent, or Firm* — TraskBritt

(57) ABSTRACT

An artificial intelligence self-learning-based static electrocardiography analysis method and apparatus, the method comprising data preprocessing, heartbeat detection, heartbeat classification based on a depth learning method, heartbeat verification, heartbeat waveform feature detection, measurement and analysis of electrocardiography events, and finally automatic output of reporting data, realizing an automated static electrocardiograph analysis method having a complete and rapid flow. The static electrocardiography analysis method can also record modification information of an automatic analysis result, collect modified data, and feed same back to the depth learning model to continue training,
(Continued)

thereby continuously making improvements and improving the accuracy of the automatic analysis method.

15 Claims, 5 Drawing Sheets

(51) Int. Cl.
    *A61B 5/352*      (2021.01)
    *A61B 5/364*      (2021.01)
    *A61B 5/366*      (2021.01)

(52) U.S. Cl.
    CPC .......... *A61B 5/7203* (2013.01); *A61B 5/7225* (2013.01); *A61B 5/7267* (2013.01); *A61B 5/7271* (2013.01)

(56) References Cited

FOREIGN PATENT DOCUMENTS

| | | |
|---|---|---|
| CN | 106214123 A | 12/2016 |
| CN | 107358196 A | 11/2017 |
| CN | 106108889 B | 11/2019 |
| CN | 106214145 B | 12/2019 |
| WO | 2009/005734 A2 | 1/1999 |

OTHER PUBLICATIONS

Acharya et al., Automated Detection of Arrhythmias Using Different Intervals of Tachycardia ECG Segments with Convolutional Neural Network, Information Sciences, Apr. 2017, 22 pages.

Chinese First Office Action for Chinese Application No. 201711203758.5 dated Dec. 24, 2019, 5 pages.

International Search Report for International Application No. PCT/CN2018/072362 dated Sep. 4, 2018, 2 pages.

International Written Opinion for International Application No. PCT/CN2018/072362 dated Sep. 4, 2018, 3 pages.

Duisterhout et al., A Computer Program for ECG Classification According to the Minnesota code, J. Electrocardiology, vol. 10, No. 4, (1977), pp. 379-386.

Extended European Search Report for Application. 11882222, dated Jun. 14, 2021, 12 pages.

* cited by examiner

ARTIFICIAL INTELLIGENCE SELF-LEARNING-BASED STATIC ELECTROCARDIOGRAPHY ANALYSIS METHOD AND APPARATUS

CROSS-REFERENCE TO RELATED APPLICATIONS

This application is a national phase entry under 35 U.S.C. § 371 of International Patent Application PCT/CN2018/072362, filed Jan. 12, 2018, designating the United States of America and published as International Patent Publication WO 2019/100566 A1 on May 31, 2019, which claims the benefit under Article 8 of the Patent Cooperation Treaty to Chinese Patent Application Serial No. 201711203758.5, filed Nov. 27, 2017.

TECHNICAL FIELD

The present disclosure relates to the technical field of artificial intelligence data analysis, and more particularly, to an artificial intelligence self-learning-based resting electrocardiogram analysis method and apparatus.

BACKGROUND

In 1908, Einthoven began to use electrocardiogram (ECG) to monitor electrophysiological activities of a heart. At present, noninvasive ECG examination has become one of important methods for diagnosis and screening of heart diseases in clinical cardiovascular field. ECG examination may be divided into several categories such as resting ECG, ambulatory ECG and exercise ECG according to clinical application. The resting ECG adopts 12-lead system (standard lead system) invented by Einthoven-Wilson-Goldberger to analyze ECG signals recorded for 8-30 seconds, which has a positive value for diagnosis and analysis of various arrhythmias and conduction block, and is the earliest, most commonly used and most basic diagnosis method in the diagnosis of coronary heart disease.

The resting ECG analysis device mainly includes three parts: ECG signal acquisition recorder, lead system and computer analysis software. The signal acquisition recorder is responsible for acquiring, measuring and recording ECG data of patients. Due to the fact that patients are easily interfered by various external factors during the ECG examination, requirements for frequency response, sample frequency, resolution, impedance, and anti-interference performance of signal acquisition are relatively high. Waveforms of resting ECG signals collected by a high-performance ECG recorder have a high signal-to-noise ratio and high signal fidelity, which is very helpful for subsequent analysis and calculation. The lead system includes electrode plates and lead wires. The analysis and calculation software performs arrhythmia analysis, long intermittent arrest, flutter and fibrillation, conduction block, premature beat and escape beat, bradycardia, tachycardia, ST segment change detection, and analysis and classification of ECG events on collected digital signals, and helps doctors to analyze and report.

The resting ECG generally uses a standard 12-lead system, including three limb leads I, II and III, six chest leads V1-V6, and three augmented leads aVR, aVL and aVF. Since data of the four leads III, aVR, aVL and aVF may be calculated according to a relationship of ECG vectors, the general resting ECG device only measures and collects data of remaining eight leads, and then calculates data of the four leads III, aVR, aVL and aVF, respectively, through an ECG vector formula.

The analysis of the resting ECG includes the following steps: firstly, signal filtering processing is performed, and then the most significant P-QRS-T complex features in heart beats are detected and identified; secondly, for identified QRS complex, P wave, T wave, R-R interval, P-R interval, ST segment and other characteristic signals, the heart beats are classified according to cardiac electrophysiological activities; and finally, combined with the classification of the heart beats and rhythmic characteristics of the heart beats, some regular continuous activities of the heart beats are further summarized as ECG events. ECG specialists analyze and describe the resting ECG examination of patients according to the classification of the heart beats and the ECG events.

Signals generated by the electrophysiological activities of heart cells are weak (millivolt level), normal ECG signals have a frequency range of 0.01 Hz-100 Hz, in which 90% of the energy is concentrated in a range of 0.25 Hz-35 Hz. Main interference signals of the resting ECG in the detection process include: power line interference (an interference including 50 Hz and its harmonics generated by human capacitances, equipment circuits, leads and the like), electromyography interference (usually, an irregular 5-2000 Hz high-frequency interference caused by muscle activities), baseline drift (which is caused by poor electrode contact, skin impedance, respiratory movement, etc., the frequency range is generally between 0.05 Hz and 2.00 Hz, which is very close to frequency components of the ST segment and PQ wave of the ECG signals).

Although patients are assisted by doctors and nurses in the process of the resting ECG examination, which may effectively reduce the influence of signal interference and ensure the stable and reliable ECG signals collected and output by the resting ECG, current computer analysis methods of the resting ECG still have the following problems: Firstly, the P wave and the T wave cannot be accurately identified in feature extraction for the heart beats. There are often excessive detection and missed detection in heart beat detection. For some special ECG signals, such as tall T waves of patients with slow heart rhythm or signals of T wave hypertrophy, the excessive detection is often easy to occur. Secondly, the classification of the heart beats basically stays in three types of sinus, supraventricular and ventricular, which is far from meeting complicated and comprehensive analysis requirements of clinical ECG doctors. Thirdly, atrial flutter and atrial fibrillation, and ST-T changes cannot be accurately identified, and the help of ST segment and T wave changes on myocardial ischemia analysis cannot be accurately analyzed. Fourthly, the identification of the heart beats and ECG events is not accurate and comprehensive, the heart beats and ECG events are easily missed due to the influence of many previous factors and will also affect the interpretation of doctors. Fifthly, due to the problems mentioned above, it is impossible to achieve automatic analysis and automatic report. Doctors still need to spend a lot of precious time carefully reading the resting ECG data, which cannot fundamentally help doctors to improve their analysis ability, both in quality and efficiency.

Therefore, how to help hospitals, especially a vast number of basic hospitals at all levels, effectively improve an automatic analysis level of the resting ECG by using the most advanced scientific and technological method, artificial intelligence technology, under a difficult condition that there are not enough professional doctors to interpret the resting ECG, is a difficult problem and challenge to be solved by the present disclosure.

BRIEF SUMMARY

The purpose of the present disclosure is to provide an artificial intelligence self-learning-based resting electrocardiogram analysis method and apparatus, which may automatically, quickly and completely analyze measurement data output by a resting ECG device, and obtain required report data.

To achieve the above purpose, a first aspect of embodiments of the present disclosure provides the artificial intelligence self-learning-based resting electrocardiogram analysis method, including:

receiving resting electrocardiogram data output by a resting electrocardiogram monitoring device, and converting a data format of the resting ECG data into a preset standard data format by resampling, and performing a first filtering processing on converted resting ECG data in the preset standard data format;

performing heart beat detection processing on resting ECG data processed by the first filtering processing to identify multiple pieces of heart beat data included in the resting ECG data, each of which is corresponding to a heart beat cycle, including amplitude data and starting-ending time data of corresponding P wave, QRS complex and T wave; and lead parameters of the heart beat data are determined;

combining the heart beat data to generate heart beat time sequence data based on the lead parameters and time rules; and generating heart beat analysis data according to the heart beat time sequence data;

performing feature extraction and analysis of an amplitude and time characterization data on the heart beat analysis data according to a trained heart beat classification model, to obtain primary classification information of the heart beat analysis data;

inputting the heart beat analysis data of particular heart beats in results of the primary classification information into a trained ST segment and T wave change model for identification, and determining ST segment and T wave evaluation information;

performing secondary classification processing on the heart beat analysis data according to resting ECG basic rule reference data, detailed feature information of the P wave and the T wave and the ST segment and T wave evaluation information under the primary classification information to finally obtain heart beat classification information;

according to the heart beat time sequence data and the heart beat classification information, performing heart beat waveform feature detection on the heart beat analysis data to determine feature heart beats; determining detailed feature information of the QRS complex in the feature heart beats; determining the detailed feature information of the P wave and the T wave in the feature heart beats; and calculating average waveform data and measurement values of the feature heart beats; and for data of the heart beat classification information and the average waveform data of the feature heart beats, generating and outputting ECG event data, data of the measurement values and the average waveform data of the feature heart beats according to the resting ECG basic rule reference data and a classification standard of ECG Minnesota coding.

Preferably, the generating heart beat analysis data according to the heart beat time sequence data includes:

cutting the heart beat data of each lead in the heart beat time sequence data according to a preset threshold to generate the heart beat analysis data of each lead.

Preferably, the determining the detailed feature information of the P wave and the T wave in the feature heart beats includes:

performing QRS complex signal elimination processing on the heart beat analysis data, and performing second filtering on the heart beat analysis data after the QRS complex signal elimination processing, performing data separation on the heart beat analysis data by an independent component analysis algorithm to obtain sequence data of each independent component, according to distribution characteristics of peak values of the sequence data of the independent component and a position of the QRS complex, selecting an independent component with the highest probability as corresponding P wave and T wave components, and determining direction and morphology features of the P wave and the T wave.

Preferably, the performing feature extraction and analysis of an amplitude and time characterization data on the heart beat analysis data according to a trained heart beat classification model, to obtain primary classification information of the heart beat analysis data includes:

according to a trained lead synchronous correlation classification model, performing the feature extraction and analysis of a synchronous amplitude and the time characterization data on the heart beat analysis data of each lead with a first data amount, to obtain the primary classification information of the heart beat analysis data.

Preferably, the inputting the heart beat analysis data of particular heart beats in results of the primary classification information into a trained ST segment and T wave change model for identification, and determining ST segment and T wave evaluation information includes:

inputting data of the particular heart beats in the primary classification into the trained ST segment and T wave change model according to leads in turn, performing the feature extraction and analysis of the amplitude and the time characterization data on the data of the particular heart beats of each lead to obtain ST segment and T wave change information of each lead, and determining the ST segment and T wave evaluation information, which is lead position information that indicates the ST segment and T wave corresponding to heart beat segment data occur change.

Preferably, the method further includes:

receiving modification information of the heart beat classification information; and taking modified data as training sample data for model training in the artificial intelligence self-learning-based electrocardiogram automatic analysis method.

The artificial intelligence self-learning-based resting ECG analysis method according to the embodiments of the present disclosure includes data preprocessing, heart beat detection, heart beat classification based on a deep learning method, heart beat verification, heart beat waveform feature detection, and measurement and analysis of ECG events, and the report data is finally automatically output. The method is a complete and fast process automatic analysis method for the resting ECG. The resting ECG analysis method of the present disclosure may also record modification information of automatic analysis results and collect modified data to feed back to the deep learning model for continuous training, thus continuously improving the accuracy rate of the automatic analysis method.

A second aspect of embodiments of the present disclosure provides an apparatus, the apparatus includes a memory and a processor, the memory is used for storing programs, and the processor is used for executing the first aspect and the methods in implementation manners of the first aspect.

A third aspect of embodiments of the present disclosure provides a computer program product including instructions, when the computer program product runs on a computer, the computer executes the first aspect and the methods in implementation manners of the first aspect.

A fourth aspect of embodiments of the present disclosure provides a computer readable storage medium, the computer readable storage medium stores computer programs, and when the computer programs are executed by the processor, the first aspect and the methods in implementation manners of the first aspect are implemented.

DETAILED DESCRIPTION

Figure 1:
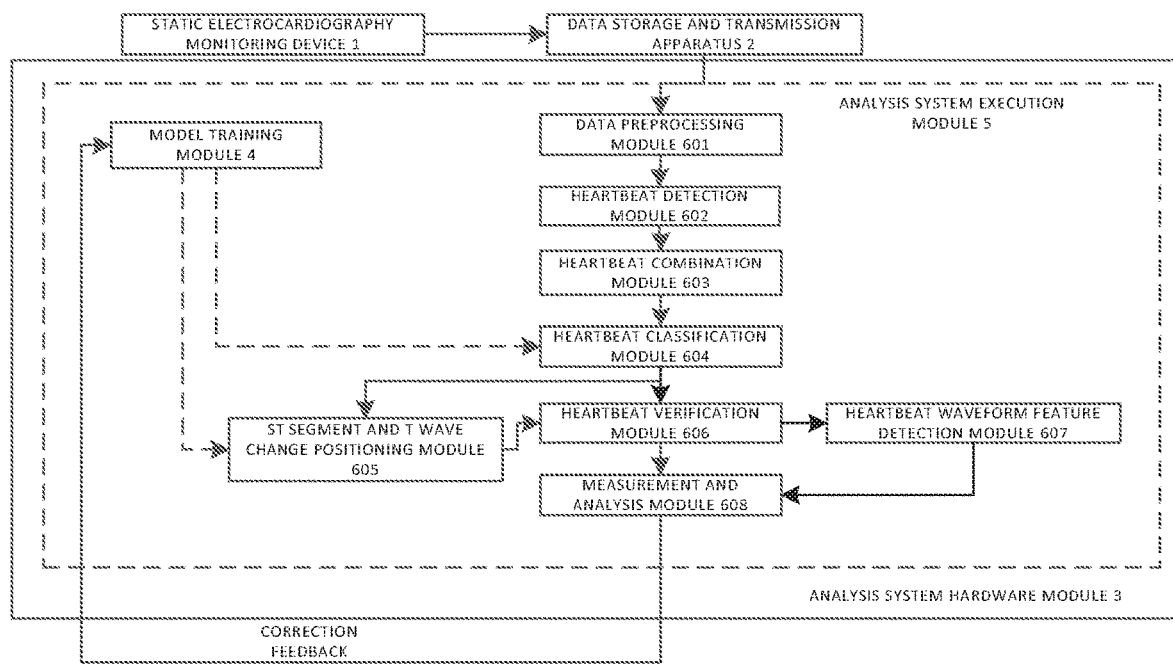
FIG. 1 is a system structure diagram illustrating an artificial intelligence self-learning-based resting electrocardiogram analysis according to an embodiment of the present disclosure.

Technical solutions of the present disclosure will be further described in detail below through accompanying drawings and embodiments.

In order to facilitate understanding of the technical solutions of the present disclosure, basic principles of artificial intelligence models, especially convolutional neural network models, are first introduced.

Artificial intelligence Convolutional Neural Network (CNN) model is a supervised learning method in deep learning, which is a multi-layer network (hidden layer) connection structure that simulates a neural network. An input signal sequentially passes through each hidden layer, in which a series of complex mathematical processes (Convolution, Pooling, Regularization, prevention of over-fitting, Dropout, Activation, and general use of Rectified Linear Unit activation function) are carried out. Some features of an object to be identified are automatically abstracted layer by layer, these features are transmitted as input to a higher hidden layer for calculation until an entire signal is reconstructed by the last several full connection layers, and Softmax function is used to perform logistics regression to achieve multi-objective classification.

CNN belongs to the supervised learning method in artificial intelligence. In a training phase, the input signal is processed through multiple hidden layers to reach last full connection layers. There is an error between a classification result obtained by Softmax logical regression and a known classification result (label). One of core ideas of deep learning is to continuously minimize the error through a large number of sample iterations so as to calculate and obtain parameters for connecting neurons in each hidden layer. In this process, it is generally necessary to construct a special cost function, and quickly and effectively minimize all connection parameters in a neural network structure with complex depth (number of hidden layers) and breadth (dimension of features) by using a nonlinearly optimized gradient descent algorithm and an error back propagation (BP) algorithm.

In deep learning, images needed to be identified are input into a training model, and finally an identification result is output after the images pass through a first hidden layer, a second hidden layer and a third hidden layer. Features with different degrees of abstraction are extracted in each layer, and finally specific categories of the images are identified, such as cars, people or animals.

An algorithm model of deep learning is very complex in mathematics. Developing a complete algorithm program requires strong professional background knowledge and rich work experience. In recent years, companies such as GOOGLE®, Microsoft, Baidu, Facebook and some famous universities (such as University of California, Berkeley, and University of Montreal in Mayada) have also successively developed and launched open source platforms for artificial intelligence development with different characteristics, helping some research and development companies in the field of deep learning to quickly master this cutting-edge technology. Among them, Caffe of Berkeley and Tensorflow of GOOGLE® are currently the two most widely used framework tools.

The model of deep learning is extremely complex, and training data needed is from hundreds of thousands, millions to tens of millions, coupled with repeated loop iterations, resulting in a very large amount of nonlinear optimized calculation. For an actual project, it often takes from a dozen hours to several days or even longer to calculate by using a central processing unit of a common computer. In this case, Graphics Processing Unit (GPU) replaces it to greatly speed up the calculation. At present, GPU cards provided by Nvidia company, due to powerful graphics and computer vision computing capabilities, a large number of computing database such as linear algebra, and supporting of parallel processing, may meet the computing of various methods with deep learning needs, and becomes a basic hardware for high-performance training and inference of current artificial intelligence.

An artificial intelligence self-learning-based resting electrocardiogram analysis method of the present disclosure is implemented based on the CNN model.

The artificial intelligence self-learning-based resting electrocardiogram analysis method provided by the embodiments of the present disclosure is implemented based on a system architecture shown in FIG. 1. The system architecture includes a resting ECG monitoring device 1, a data storage and transmission apparatus 2, an analysis system hardware module 3, a model training module 4 and an analysis system execution module 5. The analysis system execution module 5 specifically includes a data preprocessing module 601, a heart beat detection module 602, a heart beat combination module 603, a heart beat classification module 604, a ST segment and T wave change location module 605, a heart beat verification module 606, a heart beat waveform feature detection module 607, and a measurement and analysis module 608. A process of the artificial intelligence self-learning-based resting electrocardiogram analysis of the present disclosure is realized through the analysis system hardware module 3, the model training module 4 and the analysis system execution module 5 in the system architecture.

Figure 2:
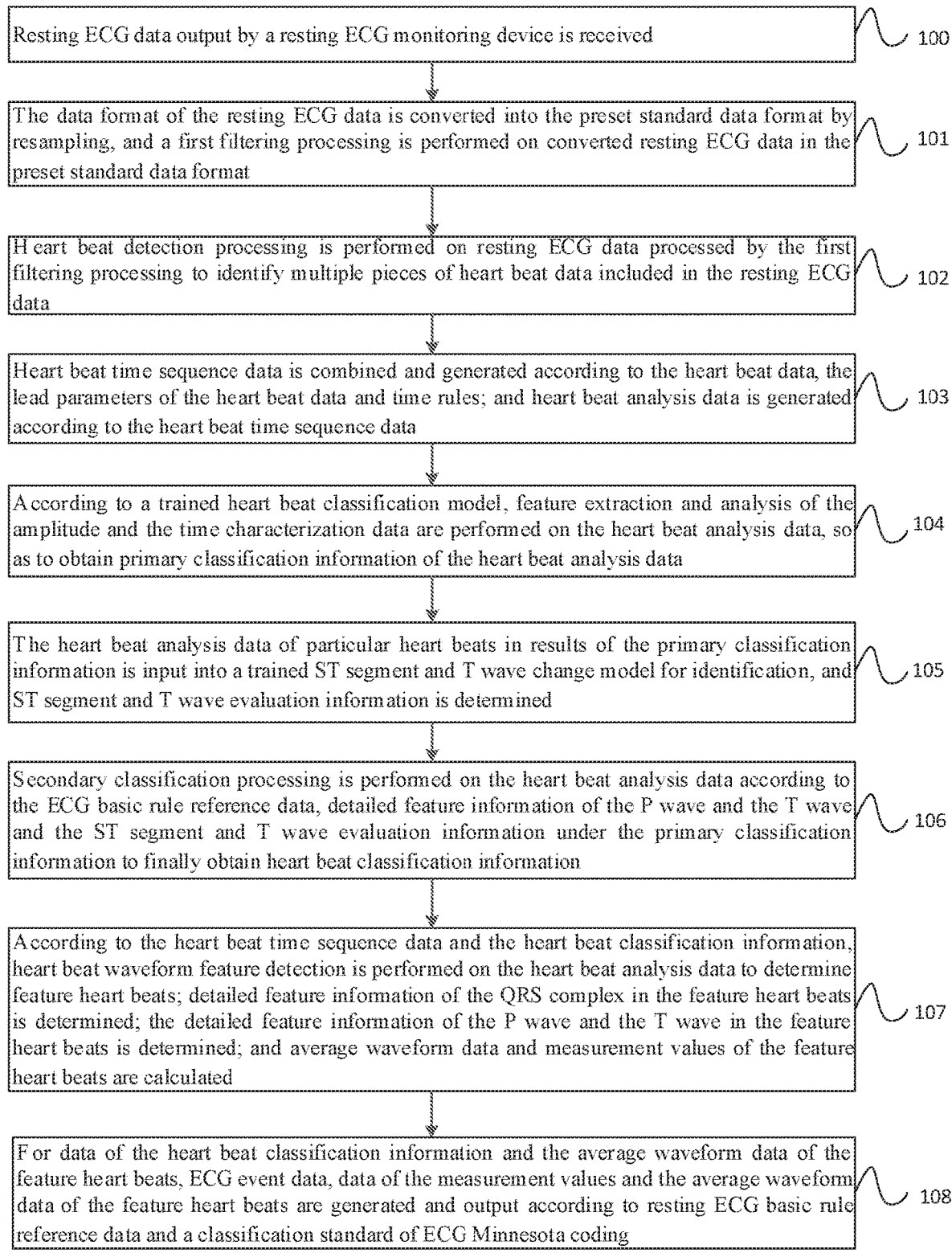
FIG. 2 is a flowchart illustrating an artificial intelligence self-learning-based resting electrocardiogram analysis method according to an embodiment of the present disclosure.

Based on the system architecture of FIG. 1 and in combination with FIG. 2, the artificial intelligence self-learning-based resting electrocardiogram analysis method of the present disclosure will be described below.

The method includes the following steps:

Step 100: resting ECG data output by a resting ECG monitoring device is received.

Specifically, electrical signals of the resting ECG are converted into digital signals by the resting ECG monitoring device for output, which may be time sequence data of standard 12-lead or other lead systems measured, collected and output by the resting ECG device, or the resting ECG data is obtained through a database or other file manners. Original data is stored by the data storage and transmission apparatus, and it may be transmitted to the analysis system hardware module through WIFI, Bluetooth, USB, 3G/4G/5G mobile communication networks, Internet of Things and other means, and is input into the analysis system execution module as input signals.

As resting ECG time sequence data for recording resting ECG graphics, due to differences in the acquisition of analog circuits, filters, and sample rates of resting ECG devices from different device manufacturers, the generated resting ECG time sequence data has great differences in lead labels, data encoding formats, gains, precision, data length per second, baseline positions and the like, and data preprocessing needs to be carried out. All input resting ECG time sequence data is processed uniformly according to requirements of the analysis process of the present disclosure and stored according to a preset standard data format. The preset standard data format refers to a data format may support data identification for the whole process of data processing. The preset standard data format refers to a data format may support data identification for the whole process of data processing.

Step 101: the data format of the resting ECG data is converted into the preset standard data format by resampling, and a first filtering processing is performed on converted resting ECG data in the preset standard data format.

The data preprocessing module executes the format adaptive to be read, resampling, filtering, and storing in a standard data format for the resting ECG data. The format of the resting ECG data adaptive to be read, has different readings implemented for different devices, and a baseline needs to be adjusted and the resting ECG data needs to be converted into millivolt data according to a gain after reading. The resting ECG data is resampled to convert the data at a sample frequency at which the whole process may process. Then, high frequency, low-frequency noise interference and baseline drift are eliminated by the filtering to improve the accuracy of artificial intelligence analysis. The processed resting ECG data is stored in the preset standard data format.

Through this step, differences in the lead, sample frequency and transmission data format used by different resting ECG devices may be eliminated, and the high frequency, low-frequency noise interference and baseline drift may be removed by digital signal filtering.

In a specific example, a resample frequency may be 200 Hz to ensure that a data length of each fixed time range is consistent in calculation, training and reasoning, so that a relatively satisfactory analysis result may be obtained without excessively increasing the complexity and time of calculation and training. Certainly, as sample rates of the resting ECG devices themselves gradually increase, GPU computing performance continues to rise and the cost decreases, and artificial intelligence algorithms continue to innovate and optimize, the sample frequency may further be improved.

The digital signal filtering may adopt a high-pass filter, low-pass filter and median filtering, respectively, to eliminate power line noise, electromyogram noise and baseline drift noise, so as to avoid the impact on subsequent analysis.

More specifically, a low-pass, high-pass Butterworth filter may be used for zero-phase shift filtering to eliminate the baseline drift and high-frequency noise, and to retain effective ECG signals. The median filtering may replace an amplitude of a sequence in a center of a window with a median of voltage amplitudes of data points in a sliding window of a preset length of time, therefore a low-frequency baseline drift may be eliminated.

Step 102: heart beat detection processing is performed on the resting ECG data processed by the first filtering processing to identify multiple pieces of heart beat data included in the resting ECG data.

Each of the multiple pieces of heart beat data corresponds to a heart beat cycle, including amplitude data and starting-ending time data of corresponding P wave, QRS complex and T wave. Heart beat detection performed by the heart beat detection module includes QRS complex detection, P wave and T wave detection. The QRS complex detection includes two processes: one is signal processing, extracting characteristic frequency bands of the QRS complex from the resting ECG data processed by the first filtering processing, and the other is to determine occurrence time of the QRS complex by setting a reasonable threshold. The ECG normally includes components of P wave, QRS complex and T wave, and a noise component. Generally, the QRS complex has a frequency range of 5 Hz to 20 Hz, so signals of the QRS complex may be extracted by a band-pass filter in this range. However, frequency bands of the P wave, the T wave, and the noise are partially overlapped with the QRS complex, so signals of non QRS complex may not be completely removed by the signal processing. Therefore, it is necessary to extract a position of the QRS complex from a signal envelope by setting a reasonable threshold. The specific detection process is a process based on peak detection. Threshold judgment is sequentially performed for each peak in the signals, and when the threshold is exceeded, a judgment process of the QRS complex is executed to detect more features, such as RR interval, morphology, etc.

Due to an instability characteristic of heart beat signals in time domain during a process of recording the resting ECG, the amplitude and frequency of the heart beat signals constantly change, and this characteristic is stronger in a disease state. When the threshold is set, a threshold adjustment needs to be dynamically performed according to the change of data characteristics in the time domain. In order to improve the accuracy and positive rate of the detection, the QRS complex detection is mostly carried out by using a double amplitude threshold combined with a time threshold. A high threshold has a high positive rate and a low threshold has a high sensitivity rate. When the RR interval exceeds a certain time (time threshold), the low threshold is used for detection to reduce missed detection. However, the low threshold is susceptible to T wave and electromyography noise due to its low threshold, which is easy to cause excessive detection. Therefore, the high threshold is preferred for detection.

There are lead parameters for heart beat data of different leads, to characterize which lead the heart beat data belongs to. Therefore, in this step, the lead parameters of the heart beat data are also determined.

Step 103: heart beat time sequence data is combined and generated according to the heart beat data, the lead parameters of the heart beat data and time rules; and heart beat analysis data is generated according to the heart beat time sequence data.

Due to the complexity of the ECG signals and the fact that each lead may be affected by different degrees of interference, there may be excessive detection and missed detection when the heart beat detection depends on a single lead. Time characterization data of heart beat results detected by different leads is not aligned. Therefore, the heart beat data of all leads needs to be combined according to results of interference identification and the time rules to generate complete heart beat time sequence data, and the time characterization data of the heart beat data of all leads is unified. The time characterization data is used to represent time information of each data point on a time axis of ECG data signals. In the subsequent analysis and calculation, according to the unified heart beat time sequence data, the heart beat data of each lead may be cut with the preset threshold, so as to generate the heart beat analysis data of each lead required for specific analysis.

Specifically, the process of combining the heart beat data performed by the heart beat combination module is as follows: a time characterization data combination of the heart beat data of different leads is obtained according to a refractory period of ECG basic rule reference data, the heart beat data with a large deviation is discarded, the time characterization data combination is voted to generate a position of a combined heart beat, and the position of the combined heart beat is added to the combined heart beat time sequence. It returns to a next group of heart beat data to be processed, and repeats until combination of all heart beat data is finished.

The refractory period of the ECG activities may preferably be between 200 ms and 280 ms. The time characterization data combination of the heart beat data of different leads obtained should meet the following conditions: each lead in the time characterization data combination of the heart beat data includes at most the time characterization data of one piece of heart beat data. When the time characterization data combination of the heart beat data is voted on, it is determined by a percentage of a number of leads with detected heart beat data in a number of effective leads. If a position of the time characterization data of the heart beat data corresponding to a lead is a low voltage segment, an interference segment and electrode peeling off, the lead is considered as an invalid lead for the heart beat data. The specific position of the combined heart beat may be calculated and obtained by using an average value of the time characterization data of the heart beat data. During the combining process, the refractory period is set in this method to avoid erroneous combining.

In this step, the unified heart beat time sequence data is output through combining. This step may simultaneously lower excessive detection and missed detection rates of the heart beat, and effectively improve the sensitivity and positive predictivity of the heart beat detection.

Step 104: according to a trained heart beat classification model, feature extraction and analysis of the amplitude and the time characterization data are performed on the heart beat analysis data, so as to obtain primary classification information of the heart beat analysis data.

Since there are differences in signal measurement, acquisition, output lead data and other aspects for different resting ECG devices, and actual application scenes are different, the heart beat classification module of the present disclosure adopts a lead synchronous correlation classification method to classify the heart beats. The lead synchronous correlation classification method is a method for synchronous correlation and analysis of the heart beat analysis data of each lead.

The lead synchronous correlation classification method may include: according to the heart beat time sequence data, cutting is performed on the heart beat data of each lead with a first data amount to generate the heart beat analysis data of each lead; and then, according to a trained lead synchronous correlation classification model, the feature extraction and analysis of a synchronous amplitude and the time characterization data are performed on the heart beat analysis data of each lead, so as to obtain the primary classification information of the heart beat analysis data.

An input of the synchronous correlation classification method of the heart beat data is data of all leads of the resting ECG device, and data points with a same position and a certain length of each lead are intercepted according to unified heart beat positions of the heart beat analysis data, and are synchronously delivered to a trained artificial intelligence deep learning model for calculation and analysis, and an output is that an accurate heart beat classification in which ECG signal characteristics of all lead and heart rhythm characteristics correlated with the heart beat in time are comprehensively considered at each heart beat position.

In this method, it is fully considered the data of different leads of the resting ECG is, actually measuring information flow of heart electrical signals transmitted in the directions of different ECG axis vectors, and multi-dimensional digital characteristics transmitted by the resting ECG signal in time and space are comprehensively analyzed, so it effectively overcomes the defect that the traditional method only relies on independent analyses of a single lead, and then results are accumulated to conduct some statistical voting methods through which classification errors are easily obtained, and greatly improves the accuracy of the heart beat classification.

The heart beat classification model in this step is obtained by training 17 million data samples of 300,000 patients in a training set. These samples are generated by accurately labeling the data according to requirements of ECG analysis and diagnosis. Labeling is mainly for common arrhythmias, conduction block, ST segment and T wave changes, which may meet model training in different application scenes. Specifically, labeled information is stored in a preset standard data format. In the preprocessing of training data, in order to increase the generalization ability of the model, small sliding is made for a classification with a small sample size to expand the data. Specifically, the data is moved 2 times based on each heart beat according to a certain step (such as 10-50 data points), so that the data may be increased by 2 times, and the recognition accuracy of classification samples with a small amount of data is improved. The generalization ability has also been verified to be improved from the actual result.

In an actual training process, two GPU servers are used for dozens of round-robin training. After the training converges, 5 million pieces of independent test data are used for testing, and the accuracy rate may reach 91.92%.

An interception length of the training data may be from 1 second to 10 seconds. For example, a sample rate is 200 Hz, a sample length is 2.5s, an obtained data length is a segment D[500] of 500 ECG voltage values (millivolts), and input data is: InputData (i, j), wherein i is a i-th lead, and j is a j-th segment of the i-th lead. All input data is randomly scattered before training, which ensures convergence of the training process. At the same time, collection of too many samples from the ECG data of a same patient is limited, which improves the generalization ability of the model, that is, an accuracy rate in a real scene. During the training, segment data D corresponding to all leads is synchronously input, and lead data of multiple spatial dimensions (different ECG axis vectors) of each time position is synchronously learned according to a multi-channel analysis method of image analysis, so that a more accurate classification result than a conventional algorithm is obtained.

Figure 3:
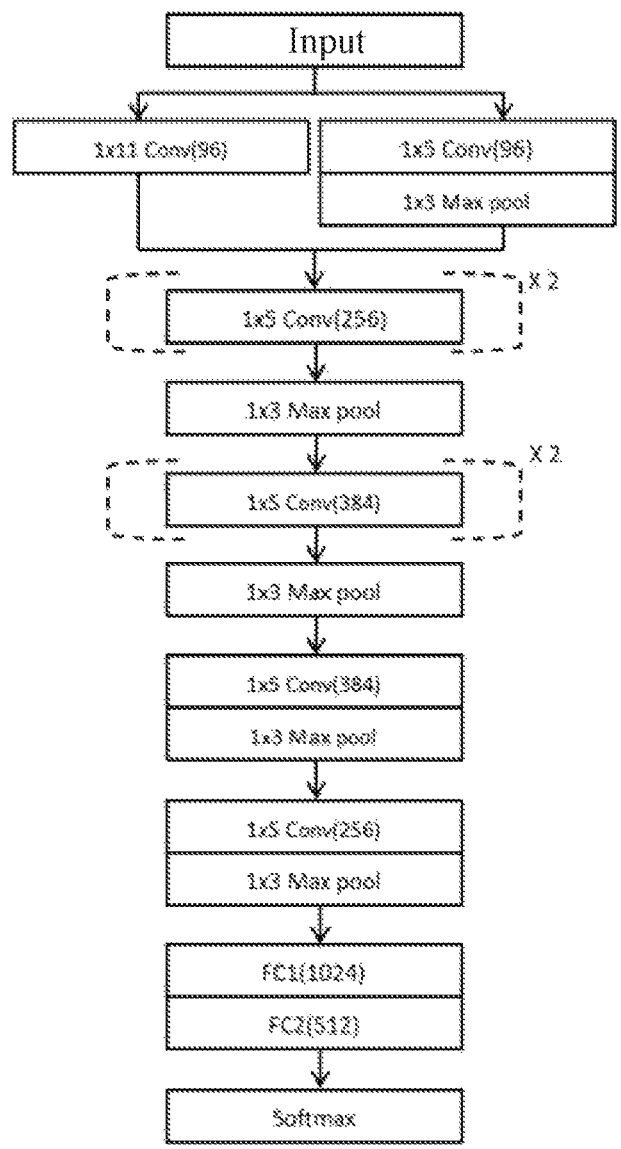
FIG. 3 is a schematic diagram illustrating a heart beat classification model according to an embodiment of the present disclosure.

As shown in FIG. 3, it is the heart beat classification model adopted in this step may, and it specifically may be an end-to-end multi-label classification model inspired by CNN models based on artificial intelligence deep learning such as AlexNet, VGG16, Inception. Specifically, the network of this model is a seven-layer convolution network, and each convolution is followed by an activation function. A first layer is a convolution layer having two different scales, followed by six convolution layers. The number of convolution kernels of the seven-layer convolution are 96, 256, 256, 384, 384 and 256, respectively. Except for the convolution kernel of the first layer, which has two scales of 5 and 11, the convolution kernels of other layers have a scale of 5. Third, fifth, sixth and seventh convolution layers are followed by a pooling layer. Finally, two full connection layers follow.

Step 105: the heart beat analysis data of particular heart beats in results of the primary classification information is input into a trained ST segment and T wave change model for identification, and ST segment and T wave evaluation information is determined.

Wherein, the ST segment and T wave evaluation information is lead position information that the ST segment and T wave corresponding to the heart beat analysis data is changed. In clinical diagnosis, changes for the ST segment and T wave are required to be located to a specific lead.

Wherein, the data of the particular heart beats of the primary classification information refers to the heart beat analysis data including sinus heart beat (N) and other heart beat types that may include ST segment changes.

Figure 5:
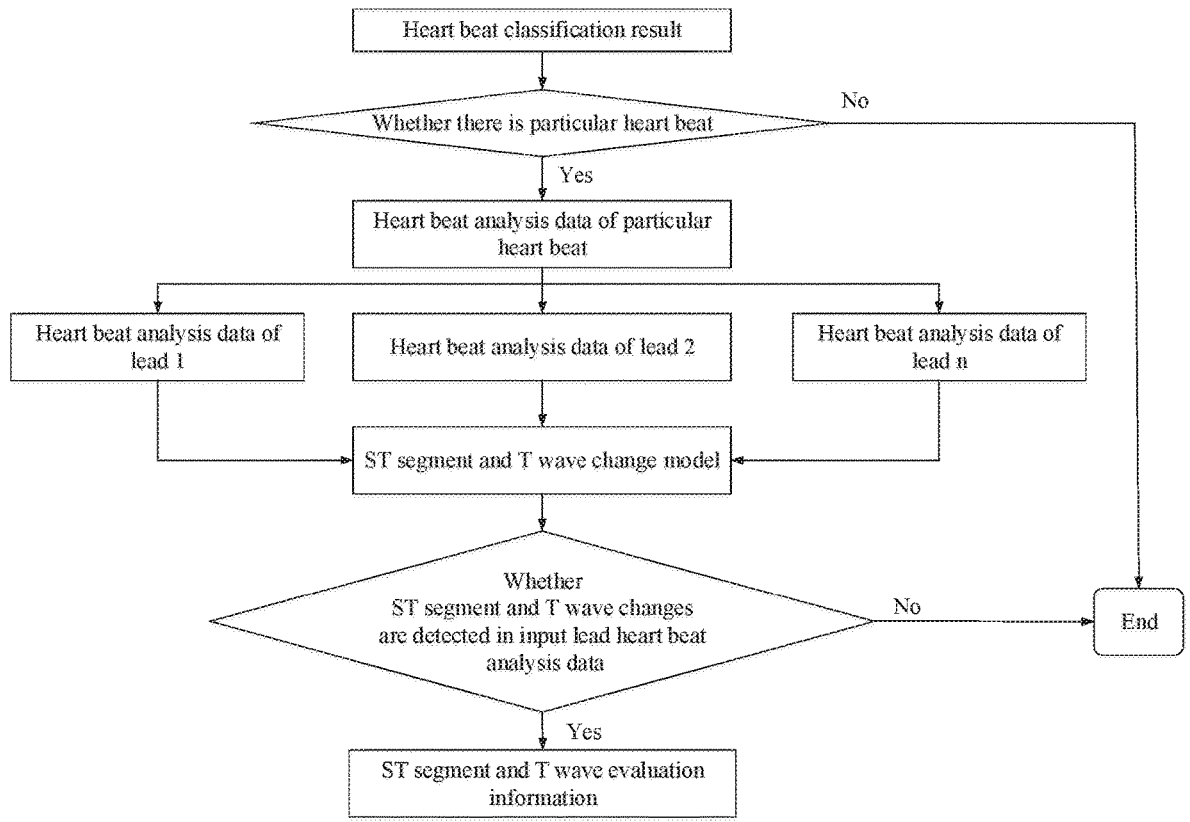
FIG. 5 is a flowchart illustrating a ST segment and T wave change location analysis according to an embodiment of the present disclosure.

The data of the particular heart beats in the primary classification information is input into a trained artificial intelligence deep learning model for identifying the ST segment and T wave changes according to each lead in turn by the ST segment and T wave change location module, and calculation and analysis is performed. An output result indicates whether features of lead segments conform to the conclusion that ST segment and T wave change, so that the information of leads where the ST segment and T wave changes occur may be determined, that is, the ST segment and T wave evaluation information. The specific method may be as follows: the heart beat analysis data of each lead, which is the sinus heart beat in the primary classification information, is put into the ST segment and T wave change model, and the sinus heart beat data is identified and judged one by one, so as to determine whether the sinus heart beat has characteristics of ST segment and T wave change and specific lead position information that the change occurs, and the ST segment and T wave evaluation information is determined. The schematic diagram of such process may be shown in FIG. 5.

A proportion of the heart beat with the ST segment and T wave changes in all heart beats is relatively low. In order to take into account a diversity of the training data and a balance of the amount of data in each category, a ratio of training data without ST segment and T wave changes and with ST segment and T wave changes is selected about 2:1, which ensures the good generalization ability of the model in the process of classification and avoid to appear a tendency of a category accounting for a relatively large proportion in the training data. Forms of the heart beat are diverse and different individuals show different forms, therefore, in order to make the model estimate distribution of each classification well and extract features effectively, training samples are collected from individuals of different ages, weights, genders and residential areas. In addition, since the ECG data of a single individual in a same time period is often highly similar, in order to avoid over-learning, when acquiring the data of the single individual, a small number of samples in different time periods are randomly selected from all the data. Finally, due to characteristics that the forms of the heart beat of patients have large differences between individuals and high similarity within the individual, different patients are divided into different data sets when dividing training sets and test sets, so as to prevent the data of a same individual from appearing in the training sets and test sets at the same time. Therefore, test results of the obtained model are closest to real application scenes, ensuring the reliability and universality of the model.

Figure 4:
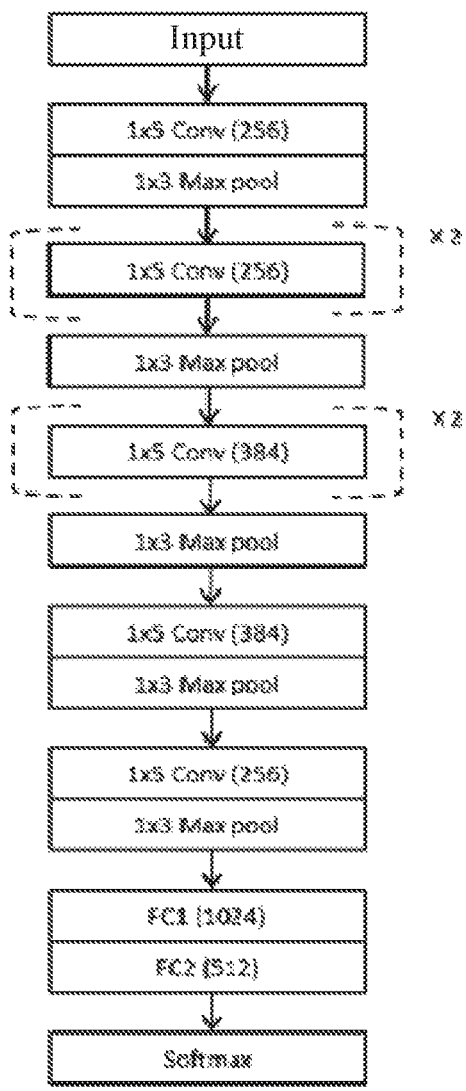
FIG. 4 is a schematic diagram illustrating a ST segment and T wave change model according to an embodiment of the present disclosure.

The ST segment and T wave change model adopted in this step may be as shown in FIG. 4, and it may be an end-to-end classification model inspired by CNN models based on artificial intelligence deep learning such as AlexNet and VGG16. Specifically, the model is a seven-layer network, which includes seven layers of convolution, five layers of pooling and two layers of full connection. A convolution kernel used in all layers of convolution is 1×5, and the number of filters for each layer of the convolution is different. The number of the filters for a first layer of convolution is 96; a second layer of convolution and a third layer of convolution are used together, and the number of the filters is 256; a fourth layer of convolution and a fifth layer of convolution are used together, and the number of the filters is 384; the number of the filters for a sixth layer of convolution is 384; the number of the filters for a seventh layer of convolution is 256. The first, third, fifth, sixth and seventh layers of convolution are followed by the layers of pooling, and then, the two layers of full connection follow. Finally, a Softmax classifier is used to divide the results into two categories. In order to increase the nonlinearity of the model and extract the features of high dimensions of the data, the mode that two layers of convolution are used together is adopted.

Step 106: secondary classification processing is performed on the heart beat analysis data under the primary classification information according to the ECG basic rule reference data, detailed feature information of the P wave and the T wave and the ST segment and T wave evaluation information to finally obtain heart beat classification information.

Specifically, the ECG basic rule reference data such as a minimum time interval between two heart beats, a minimum interval between the P wave and R wave, is generated according to the description of basic rules of cardiomyocytes electrophysiological activities and ECG clinical diagnosis in authoritative ECG textbooks, and which is used for subdividing the primary classification information after classification of the heart beat. The primary classification information after classification of the heart beat is subdivided, is mainly based on the RR interval between the heart beats and a medical significance of different heart beat signals on each lead. According to the ECG basic rule reference data combined with classification and identification of a certain number of continuous heart beats and the detailed feature information of the P wave and T wave, a classification of ventricular heart beats is divided into more detailed heart beat classifications by the heart beat verification module, including ventricular premature beat (V), ventricular escape beat (VE), ventricular tachycardia beat (VT), and supraventricular heart beats are subdivided into supraventricular premature beat (S), atrial escape beat (SE), junctional escape beat (JE) and atrial tachycardia beat (AT), etc.

In addition, through the secondary classification processing, erroneous classification identification that does not conform to the ECG basic rule reference data in the primary classification may also be corrected. The subdivided heart beat classifications are pattern matched according to the ECG basic rule reference data, classification identification, which does not conform to the ECG basic rule reference data, is found, and corrected to a reasonable classification according to the RR interval and classification labels before and after.

Specifically, after the secondary classification processing, a variety of heart beat classifications may be output, such as: normal sinus heart beat (N), complete right bundle branch block (N_CRB), complete left bundle branch block (N_CLB), intraventricular block (N_VB), first degree atrioventricular block (N_B1), pre-excitation syndrome (N_PS), ventricular premature beat (V), ventricular escape beat (VE), ventricular tachycardia beat (VT), supraventricular premature beat (S), atrial escape beat (SE), junctional escape beat (JE), atrial tachycardia beat (AT), atrial flutter/atrial fibrillation (AF) and artifact (A).

Step 107: according to the heart beat time sequence data and the heart beat classification information, heart beat waveform feature detection is performed on the heart beat analysis data to determine feature heart beats; detailed feature information of the QRS complex in the feature heart beats is determined; the detailed feature information of the P wave and the T wave in the feature heart beats is determined; and average waveform data and measurement values of the feature heart beats are calculated.

The feature heart beats are determined according to a result of the heart beat classification information. If sinus heart beats are included in the result of the heart beat classification information, the sinus heart beats are selected as the feature heart beats. Otherwise, heart beats with the most occurrence frequency are selected as the feature heart beats.

The detailed feature information of the P wave, T wave, and QRS complex are extracted by the heart beat waveform feature detection module through calculating a position of a segmentation point in the QRS complex and a position of a segmentation point of the P wave and the T wave. Wherein, the detailed feature information includes amplitudes, directions, morphology and segmentation point time of the QRS complex, the P wave and the T wave. At the same time, the average waveform, ECG axis, QT interval and other measurement values of the feature heart beats are calculated. Specifically, the measurement values are measurement parameters required in the clinical diagnostic standard of the resting ECG.

It may be realized by QRS complex segmentation point detection, PT detection algorithms and heart beat signal feature algorithms, respectively.

The QRS complex segmentation point detection: according to a segment power maximum point and starting and ending points of the QRS complex provided by QRS complex detection algorithms, a R point, R' point, S point and S' point of the QRS complex in the lead are searched, a median of each segmentation point is calculated as the final position of the segmentation point.

The PT detection algorithms: since each wave in a heart beat is generated at same time, but has different space distribution, while the noise has different time and space distribution, the P and T waves may be detected by tracing algorithms. Firstly, QRS complex elimination processing is performed on the signals and low-pass filtering is performed to remove interference, and then individual independent components of an original waveform are calculated by an independent component analysis algorithm. In separated individual independent components, corresponding components are selected as P wave and T wave signals according to distribution characteristics of peaks and the position of the QRS complex, and the direction and morphology features of the P wave and the T wave are determined.

The heart beat signal feature algorithms: One important detection of the resting ECG is involved with the measurement of heart beat signal features, which includes the calculation of the average waveform of the feature heart beats, the calculation of the ECG axis and time relationships between various segmentation points. The average waveform of the feature heart beats is obtained by aligning the heart beat signals of all feature heart beats according to the R point and then averaging their median values, and further the measurement values such as ECG axis, QT interval, QTc interval are calculated.

Step 108: for data of the heart beat classification information and the average waveform data of the feature heart beats, ECG event data, data of the measurement values and the average waveform data of the feature heart beats are generated and output according to resting ECG basic rule reference data in conformity with a classification standard of ECG Minnesota coding.

Specifically, the measurement and analysis module generates a classification result of the ECG event corresponding to the ECG event data through calculation and classification, including but not limited to:

Within a normal range, sinus rhythm, poor recording, left and right hand electrodes reversed, counterclockwise rotation, clockwise rotation, low potential difference (limb leads), low potential difference (chest leads), sinus bradycardia, sinus tachycardia, tachycardia, bradycardia, extreme tachycardia, extreme bradycardia, sinus arrhythmia, atrial escape beat, junctional escape beat, ventricular escape beat, atrial escape rhythm, junctional escape rhythm, ventricular escape rhythm, supraventricular premature contraction, ventricular premature contraction, supraventricular premature contraction trigeminy, ventricular premature contraction trigeminy, frequent supraventricular premature contraction, frequent ventricular premature contraction, supraventricular premature contraction bigeminy, ventricular premature contraction bigeminy, supraventricular tachycardia, ventricular tachycardia, two episodes of supraventricular premature contraction, two episodes of ventricular premature contraction, non-paroxysmal supraventricular tachycardia, atrial fibrillation, atrial flutter, ventricular arrest, sinus arrest, atrial flutter-atrial fibrillation with complete right bundle branch block, sinoatrial block, second-degree type I sinoatrial block, sinoatrial block (Mobitz), first-degree atrioventricular block, second-degree atrioventricular block (Wenckbach), second-degree atrioventricular block (Mobitz), third-degree atrioventricular block, artificial pacemaker rhythm, incomplete right bundle branch block, intraventricular block, complete right bundle branch block, complete left bundle branch block, QT prolongation, QT shortening, T wave change, ST segment elevation, ST segment depression, unidentifiable ECG axis, slight left ECG axis deflection, right ECG axis deflection, obvious right ECG axis deflection, left ECG axis deflection, left ventricle is high potential, V1 is positive T wave, right ventricle hypertrophy, left atrial enlargement, right atrial enlargement, right ventricle hypertrophy and right atrial enlargement, right ventricle hypertrophy and left atrial enlargement, left ventricle hypertrophy and left atrial enlargement, left ventricular hypertrophy, P-R interval shortening, P-R interval prolongation, WPW syndrome, WPW syndrome (type A), WPW syndrome (type B), negative T wave, poor R wave rise, abnormal Q wave, anterior wall infarction, lateral wall infarction and inferior wall infarction.

At the same time, the measurement and analysis module further calculates the following data of the measurement values, but not limited to:

heart rate, P-R interval, QT interval, QTc interval, ECG axis, RV5, SV1, and R+S.

Finally, the ECG event data, the data of the measurement values, and heart beat waveform feature data are generated and output.

In the present disclosure, in addition to the above process, manual check may also be performed based on obtained classification results, and the checked heart beat classification data, which is not in conformity with classification results output by automatic analysis, is corrected, and fed back and input into to the trained model as training samples for artificial intelligence self-learning. The deep learning model may continuously carry out iterative loop training by inputting new training data, thereby continuously improving the accuracy of two classification models (the heart beat classification model, and the ST segment and T wave change model) used by the present disclosure.

It should be noted that, although specific implementation manners of the three classification models are specifically described in the above-mentioned steps, it is not limited that the specific implementation may only be realized by the illustrated manners. All three models may be implemented by one or more of LeNet-5 model, AlexNet model, VGG16 model and Inception model, and other models such as ResNet model, RNN-related model, Auto-Encoding model or SeqToSeq model may also be used for training and classification inferring, and the number of categories classified by the models, and recognized ECG event types and heart rate parameters for statistical analysis are not limited.

Figure 6:
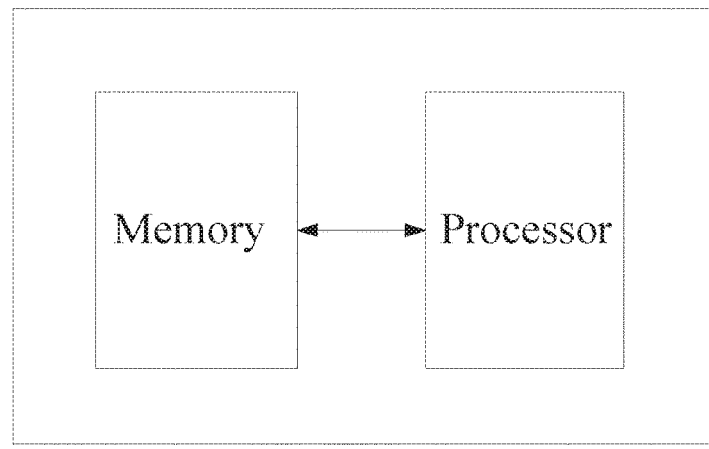
FIG. 6 is a schematic structure diagram illustrating an artificial intelligence self-learning-based resting electrocardiogram analysis apparatus according to an embodiment of the present disclosure.

FIG. 6 is a schematic structure diagram illustrating an apparatus according to an embodiment of the present disclosure. The apparatus includes a processor and a memory. The memory may be connected to the processor via a bus. The memory may be a non-volatile memory, such as a hard disk drive and a flash memory, in which software programs and device drivers are stored. The software programs may perform various functions of the above method provided by the embodiment of the present disclosure. The device drivers may be a network and interface drivers. The processor is used for executing the software programs, and when the software programs are executed, the method provided by the embodiments of the present disclosure may be realized.

It should be noted that an embodiment of the present disclosure also provides a computer readable storage medium. The computer readable storage medium stores computer programs, and when the computer programs are executed by the processor, the method provided by the embodiments of the present disclosure may be realized.

An embodiment of the present disclosure also provides a computer program product including instructions. When the computer program product runs on a computer, the processor performs the above method.

In the artificial intelligence self-learning-based resting ECG analysis method and apparatus according to the embodiments of the present disclosure, through data pre-processing, heart beat detection, heart beat classification based on a deep learning method, heart beat verification, heart beat waveform feature detection, and measurement and analysis of ECG events, the report data is finally automatically output. The method is a complete and fast process automatic analysis method for the resting ECG. The resting ECG analysis method of the present disclosure may also record modification information of automatic analysis results and collect modified data to feed back to the deep learning model for continuous training, thus continuously improving the accuracy rate of the automatic analysis method.

Those skilled in the art should further realize that the units and algorithm steps of the examples described in the embodiments disclosed herein may be implemented in electronic hardware, computer software, or a combination of the two. In order to clearly illustrate the interchangeability of hardware and software, the composition and steps of each example have been generally described according to functions in the above description. Whether these functions are implemented in hardware or software depends on the specific application and design constraints of the technical solutions. Those skilled in the art may use different methods to implement the described functions for each specific application, but such implementation should not be considered to be beyond the scope of the present disclosure.

The steps of methods or algorithm described in the embodiments disclosed herein may be implemented in hardware, a software module executed by a processor, or a combination of the two. The software module may be placed in random access memory (RAM), memory, read only memory (ROM), electrically programmable ROM, electrically erasable programmable ROM, registers, hard disks, removable disks, CD-ROM, or any other form of storage medium known in the technical field.

The specific embodiments described above have further explained the purpose, technical solution and beneficial effects of the present disclosure in detail. It should be understood that the above is only specific embodiments of the present disclosure and is not used to limit the scope of protection of the present disclosure. Any modification, equivalent substitution, improvement, etc., made within the spirit and principles of the present disclosure should be included in the scope of protection of the present disclosure.

What is claimed is:

1. An artificial intelligence self-learning-based resting electrocardiogram analysis method, comprising:
receiving resting electrocardiogram data output by a resting electrocardiogram monitoring device, and converting a data format of the resting ECG data into a preset standard data format by resampling, and performing a first filtering processing on converted resting ECG data in the preset standard data format;
performing heart beat detection processing on resting ECG data processed by the first filtering processing to identify multiple pieces of heart beat data comprised in the resting ECG data, each of which is corresponding to a heart beat cycle, comprising amplitude data and starting-ending time data of corresponding P wave, QRS complex and T wave; and lead parameters of the heart beat data are determined;

combining the heart beat data to generate heart beat time sequence data based on the lead parameters and time rules; and generating heart beat analysis data according to the heart beat time sequence data;

performing feature extraction and analysis of an amplitude and time characterization data on the heart beat analysis data according to a trained heart beat classification model, to obtain primary classification information of the heart beat analysis data;

inputting the heart beat analysis data of particular heart beats in results of the primary classification information into a trained ST segment and T wave change model for identification, and determining ST segment and T wave evaluation information;

performing secondary classification processing on the heart beat analysis data according to resting ECG basic rule reference data, detailed feature information of the P wave and the T wave and the ST segment and T wave evaluation information under the primary classification information to finally obtain heart beat classification information;

according to the heart beat time sequence data and the heart beat classification information, performing heart beat waveform feature detection on the heart beat analysis data to determine feature heart beats; determining detailed feature information of the QRS complex in the feature heart beats; determining the detailed feature information of the P wave and the T wave in the feature heart beats; and calculating average waveform data and measurement values of the feature heart beats; and for data of the heart beat classification information and the average waveform data of the feature heart beats, generating and outputting ECG event data, data of the measurement values and the average waveform data of the feature heart beats according to the resting ECG basic rule reference data and a classification standard of ECG Minnesota coding.

2. The resting electrocardiogram analysis method according to claim 1, wherein the generating heart beat analysis data according to the heart beat time sequence data comprises:
cutting the heart beat data of each lead in the heart beat time sequence data according to a preset threshold to generate the heart beat analysis data of each lead.

3. The resting electrocardiogram analysis method according to claim 2, wherein the determining the detailed feature information of the P wave and the T wave in the feature heart beats comprises:
performing QRS complex signal elimination processing on the heart beat analysis data, and performing second filtering on the heart beat analysis data after the QRS complex signal elimination processing, performing data separation on the heart beat analysis data by an independent component analysis algorithm to obtain sequence data of each independent component, according to distribution characteristics of peak values of the sequence data of the independent component and a position of the QRS complex, selecting an independent component with the highest probability as corresponding P wave and T wave components, and determining direction and morphology features of the P wave and the T wave.

4. The resting electrocardiogram analysis method according to claim 3, wherein the performing feature extraction and analysis of an amplitude and time characterization data on the heart beat analysis data according to a trained heart beat classification model, to obtain primary classification information of the heart beat analysis data comprises:
according to a trained lead synchronous correlation classification model, performing the feature extraction and analysis of a synchronous amplitude and the time characterization data on the heart beat analysis data of each lead with a first data amount, to obtain the primary classification information of the heart beat analysis data.

5. The resting electrocardiogram analysis method according to claim 4, wherein the inputting the heart beat analysis data of particular heart beats in results of the primary classification information into a trained ST segment and T wave change model for identification, and determining ST segment and T wave evaluation information comprises:
inputting data of the particular heart beats in the primary classification into the trained ST segment and T wave change model according to leads in turn, performing the feature extraction and analysis of the amplitude and the time characterization data on the data of the particular heart beats of each lead to obtain ST segment and T wave change information of each lead, and determining the ST segment and T wave evaluation information, which is lead position information that indicates the ST segment and T wave corresponding to heart beat segment data occur change.

6. The resting electrocardiogram analysis method according to claim 5, wherein the method further comprises:
receiving modification information of the heart beat classification information; and
taking modified data as training sample data for model training in the artificial intelligence self-learning-based electrocardiogram automatic analysis method.

7. A computer program product comprising instructions, wherein when the computer program product runs on a computer, the computer executes the method of claim 6.

8. A computer readable storage medium, comprising instructions, wherein when the instructions run on a computer, the computer executes the method of claim 6.

9. The resting electrocardiogram analysis method according to claim 1, wherein the determining the detailed feature information of the P wave and the T wave in the feature heart beats comprises:
performing QRS complex signal elimination processing on the heart beat analysis data, and performing second filtering on the heart beat analysis data after the QRS complex signal elimination processing, performing data separation on the heart beat analysis data by an independent component analysis algorithm to obtain sequence data of each independent component, according to distribution characteristics of peak values of the sequence data of the independent component and a position of the QRS complex, selecting an independent component with the highest probability as corresponding P wave and T wave components, and determining direction and morphology features of the P wave and the T wave.

10. The resting electrocardiogram analysis method according to claim 1, wherein the performing feature extraction and analysis of an amplitude and time characterization data on the heart beat analysis data according to a trained heart beat classification model, to obtain primary classification information of the heart beat analysis data comprises:
according to a trained lead synchronous correlation classification model, performing the feature extraction and analysis of a synchronous amplitude and the time characterization data on the heart beat analysis data of each lead with a first data amount, to obtain the primary classification information of the heart beat analysis data.

11. The resting electrocardiogram analysis method according to claim 1, wherein the inputting the heart beat analysis data of particular heart beats in results of the primary classification information into a trained ST segment and T wave change model for identification, and determining ST segment and T wave evaluation information comprises:
  inputting data of the particular heart beats in the primary classification into the trained ST segment and T wave change model according to leads in turn, performing the feature extraction and analysis of the amplitude and the time characterization data on the data of the particular heart beats of each lead to obtain ST segment and T wave change information of each lead, and determining the ST segment and T wave evaluation information, which is lead position information that indicates the ST segment and T wave corresponding to heart beat segment data occur change.

12. The resting electrocardiogram analysis method according to claim 1, wherein the method further comprises:
  receiving modification information of the heart beat classification information; and
  taking modified data as training sample data for model training in the artificial intelligence self-learning-based electrocardiogram automatic analysis method.

13. A computer program product comprising instructions, wherein when the computer program product runs on a computer, the computer executes the method of claim 1.

14. A computer readable storage medium, comprising instructions, wherein when the instructions run on a computer, the computer executes the method of claim 1.

15. An artificial intelligence self-learning-based resting electrocardiogram analysis method, comprising:
  receiving, at an analysis system, resting electrocardiogram data from a resting electrocardiogram monitoring device, and converting a data format of the resting ECG data into a preset standard data format by resampling, and performing a first filtering processing on converted resting ECG data in the preset standard data format;
  performing, at the analysis system, heart beat detection processing on resting ECG data processed by the first filtering processing to identify multiple pieces of heart beat data comprised in the resting ECG data, each of which is corresponding to a heart beat cycle, comprising amplitude data and starting-ending time data of corresponding P wave, QRS complex and T wave; and lead parameters of the heart beat data are determined;
  combining the heart beat data to generate heart beat time sequence data in the analysis system based on the lead parameters and time rules; and
  generating heart beat analysis data in the analysis system according to the heart beat time sequence data;
  performing, at the analysis system, feature extraction and analysis of an amplitude and time characterization data on the heart beat analysis data according to a trained heart beat classification model, to obtain primary classification information of the heart beat analysis data;
  inputting the heart beat analysis data of particular heart beats in results of the primary classification information into a trained ST segment and T wave change model for identification, and determining ST segment and T wave evaluation information;
  performing, at the analysis system, secondary classification processing on the heart beat analysis data according to resting ECG basic rule reference data, detailed feature information of the P wave and the T wave and the ST segment and T wave evaluation information under the primary classification information to finally obtain heart beat classification information;
  according to the heart beat time sequence data and the heart beat classification information, performing, at the analysis system, heart beat waveform feature detection on the heart beat analysis data to determine feature heart beats;
  determining, at the analysis system, detailed feature information of the QRS complex in the feature heart beats;
  determining the detailed feature information of the P wave and the T wave in the feature heart beats; and
  calculating, at the analysis system, average waveform data and measurement values of the feature heart beats; and
  for data of the heart beat classification information and the average waveform data of the feature heart beats, generating and outputting ECG event data, data of the measurement values and the average waveform data of the feature heart beats according to the resting ECG basic rule reference data and a classification standard of ECG Minnesota coding.

* * * * *